US010717082B2

(12) United States Patent
Tran (10) Patent No.: US 10,717,082 B2
(45) Date of Patent: Jul. 21, 2020

(54) METHOD AND DEVICE FOR SELECTIVE, SPECIFIC AND SIMULTANEOUS SORTING OF RARE TARGET CELLS IN A BIOLOGICAL SAMPLE

(71) Applicant: Phuong Lan Tran, Paris (FR)

(72) Inventor: Phuong Lan Tran, Paris (FR)

(*) Notice: Subject to any disclaimer, the term of this patent is extended or adjusted under 35 U.S.C. 154(b) by 246 days.

(21) Appl. No.: 15/526,436

(22) PCT Filed: Nov. 10, 2015

(86) PCT No.: PCT/FR2015/053051
§ 371 (c)(1),
(2) Date: May 12, 2017

(87) PCT Pub. No.: WO2016/075410
PCT Pub. Date: May 19, 2016

(65) Prior Publication Data
US 2018/0297024 A1    Oct. 18, 2018

(30) Foreign Application Priority Data
Nov. 12, 2014  (FR) ..................... 14 60912

(51) Int. Cl.
*G01N 33/543*    (2006.01)
*B01L 3/00*    (2006.01)
(Continued)

(52) U.S. Cl.
CPC ......... *B01L 3/50273* (2013.01); *B01L 3/5025* (2013.01); *B01L 3/502715* (2013.01); *B01L 9/52* (2013.01); *C12Q 1/6827* (2013.01); *G01N 33/54366* (2013.01); *B01L 2200/027* (2013.01); *B01L 2200/028* (2013.01); *B01L 2200/0621* (2013.01); *B01L 2200/0642* (2013.01);
(Continued)

(58) Field of Classification Search
None
See application file for complete search history.

(56) References Cited

U.S. PATENT DOCUMENTS

2004/0001779 A1    1/2004 Anderson et al.
2005/0009101 A1    1/2005 Blackburn
(Continued)

FOREIGN PATENT DOCUMENTS

EP    1 374 989    1/2004
WO    02/41995    5/2002

*Primary Examiner* — Paul S Hyun
(74) *Attorney, Agent, or Firm* — Clark & Brody LP (57) ABSTRACT

A device for sorting of rare target cells in a biological sample comprises a first row of at least two laminar-flow fluidic chambers, each comprising an inlet connected to a reservoir of a biological solution and an outlet and a last row of laminar-flow fluidic chambers equal in number to the number of chambers of the first row. Each last row fluidic chamber comprises an inlet connected to an outlet of a chamber of the first row and an outlet. A reservoir for collecting solution is connected to each outlet of the fluidic chambers of the second row, at least one pump causing a sample of the solution to circulate in the fluidic chambers of the first row then of the last row, wherein the fluidic chambers include a surface functionalized with molecules, at least some of which able to bond with a receptor molecule borne by the target cells.

12 Claims, 4 Drawing Sheets

(51) Int. Cl.
*B01L 9/00* (2006.01)
*C12Q 1/6827* (2018.01)

(52) U.S. Cl.
CPC . *B01L 2200/0689* (2013.01); *B01L 2300/021* (2013.01); *B01L 2300/0636* (2013.01); *B01L 2300/087* (2013.01); *B01L 2300/0822* (2013.01); *B01L 2300/0851* (2013.01); *B01L 2300/0874* (2013.01); *B01L 2300/0877* (2013.01); *B01L 2300/0887* (2013.01); *B01L 2300/12* (2013.01)

(56) References Cited

U.S. PATENT DOCUMENTS

| | | |
|---|---|---|
| 2006/0215155 A1 | 9/2006 | Weber |
| 2009/0081808 A1* | 3/2009 | Burmeister ........ G01N 21/6428 436/501 |
| 2012/0028342 A1* | 2/2012 | Ismagilov ......... B01L 3/502738 435/283.1 |
| 2014/0194305 A1* | 7/2014 | Kayyem ........... B01L 3/502715 506/9 |

* cited by examiner

METHOD AND DEVICE FOR SELECTIVE, SPECIFIC AND SIMULTANEOUS SORTING OF RARE TARGET CELLS IN A BIOLOGICAL SAMPLE

The invention relates to a process and a device for the selective, specific and simultaneous sorting of rare target cells in a biological sample.

The general field covered by the invention is the field of detecting rare cells and their heterogeneous sub-populations in a complex biological liquid (blood, bone marrow, etc.). "Rare" cells are intended to mean target cells present in a sample at a concentration of between 1 and 10 cells per milliliter (ml) of sample comprising $10*10^9$ cells.

More specifically, the invention relates to cancer diagnosis/prognosis in the field of public health.

The mortality associated with malignant tumors is mainly due to the presence of locoregional metastases which are distant from the primary tumor. Controlling metastatic dissemination is an important factor for prognosis of the disease. The resulting applications comprise screening high-risk populations, giving predictive information on diagnosis, prognosis, treatment, and monitoring of the disease or of the response to a treatment, and optimizing a treatment or developing a novel therapy in terms of personalized molecular medicine.

Tumor cells contained in the peripheral blood (CTC), or in bone marrow niches (DTC) of patients suffering from cancer are heterogeneous and composed of sub-populations of cells of epithelial origin and non-epithelial cells: cancer stem cells (CSC), mesenchymal cells, non-hematopoietic endothelial cells (CEC), etc.

The ability to isolate, enumerate and carry out molecular characterization of disseminated tumor cells, including tumor cells of epithelial origin (CTC and DTC), tumor cells of non-epithelial origin (cancer stem cells (CSC), non-hematopoietic endothelial cells (CEC) and mesenchymal cells, etc., would contribute to improving the clinical treatment of patients suffering from cancer for early diagnosis, evaluation of the tumoral process, and therapeutic response, including resistance to treatment.

Other applications in predictive medicine target the same requirements in which, under the same conditions of cellular frequency, the invention relates to the detection and characterization of various stem cells and fetal cells in the maternal blood for antenatal diagnosis and genetic anomalies, etc.

In medical observation, the invention may be applied to monitoring patients at risk of myocardial infarction, by detecting and monitoring the change in non-hematopoietic circulating endothelial cells (CEC), to post-vaccination monitoring, to monitoring of autoimmune disorders, etc.

Among the proposed and published technologies, two types are distinguished:
I. Methods for detecting rare cells in a single step, with or without provision of a unique detection antibody;
II. Methods for detecting rare cells in two steps, involving magnetic beads (CellSearch).

Among the single-step methods (I) there are:
I-i) a technique of immunoselection by magnetic beads grafted with a unique cell recognition antibody, CellSearch, developed by Veridex, (Johnson & Johnson), and approved by the Foods and Drugs Administration (FDA) (Cristofanilli, M et al. 2004). All the studies are conducted by means of a unique antibody directed against the epithelial cell adhesion molecule (anti-EpCAM antibody);
I-ii) microfluidic systems comprising:
   a) Si microchips grafted with the anti-EpCAM antibody by M Toner's team (CTC-chip, Nagrath S. et al. 2007; Herringbone chip, Stott S L et al. 2010),
   b) a device involving magnetic beads and microfluidics to sort cells (CTC-iChip, Ozkumur E et al. 2013);
I-iii) a technique of cell separation, according to a size criterion, carried out by means of filters with 8 μm-diameter pores (Wong N S et al. 2006). This approach does not demonstrate any selectivity, given the variability in cell sizes. All tumor cells have variable sizes.
I-iv) a microfluidic platform with a nanostructure of graphene oxide functionalized with the anti-EpCAM antibody (Yoon H J et al. 2013).

Among the two-step methods (II) there are:
II-i) MagSweeper, derived from the CellSearch method using magnetic beads grafted with the anti-EpCAM antibody (Talasaz A H et al. 2009);
II-ii) a microsystem based on the rheological properties of the cells (Tang S J et al. 2009);
II-iii) a microfluidic device involving columns of magnetic beads, referred to as Ephesia (Saliba A E et al, 2010);
II-iv) a combination of leukapheresis with the CellSearch system (Fischer J C et al. 2013);
II-v) the use of dielectrophoresis associated with CellSearch, referred to as DEPArray (Peeters D J E et al. 2013).

The major technical limitation of these methods lies in a single detection and the molecular characterization of a single sub-population of tumor cells of epithelial origin (CTC and DTC) expressing the epithelial adhesion molecule EpCAM.

For this reason, none of these methods can provide a solution to the medical requirements for detection and molecular characterization of multiple heterogeneous sub-populations of cells of epithelial origin (CTC and DTC) and non-epithelial cells (CSC, mesenchymal cells, CEC, etc.).

In addition, none of the above techniques is compatible both with IF (immunofluorescence) characterization followed by FISH (fluorescence in situ hybridization) characterization.

Moreover, all these techniques require a volume of treated blood of between 5 and 10 ml, and none of them can be used with a frozen blood sample, such that they are all very restrictive in terms of use.

Finally, only the filtration technique makes it possible to detect aggregates.

However, these filtration techniques, similarly to the magnetic beads, are relatively insensitive to the detection of circulating tumor cells from a localized cancer, due to the very low concentration thereof in the blood, when they are below 30 CTC in 7.5 ml of blood (CellSearch method, Veridex). Only circulating cells from metastasized cancers can be detected by filtration techniques, because the concentration thereof in the blood is very high. These techniques therefore suffer from too low a detection capacity (approximately one cell per 5 billion cells), whereas the process according to the invention enables detection of one cell among 10 billion cells. With a view to strategies for personalized medicine, it is important that each sub-population of rare cells is characterized as a function of the criteria of therapeutic targeting and response to treatment.

The invention therefore aims to propose a device and a process for sorting target cells in a biological sample which is selective, specific, simultaneous, multipurpose, economical, industrializable, that is to say enabling automatic counting and detection, compatible both with IF characterization and FISH characterization, requiring a volume of blood which is less than 5 ml, capable of using a frozen blood sample, enabling aggregate detection, and able to be used in existing analytical instruments.

An aim of the present invention is therefore also to be able to detect cell populations and sub-populations of localized cancers circulating in the blood by virtue of targeting their detection by specific antibodies.

To this end, a subject of the invention is a mesofluidic device for the selective, specific and simultaneous sorting of rare target cells in a biological sample at a concentration of between 1 and 10 cells per milliliter (ml) of sample, characterized in that it comprises:

a first row of at least two laminar-flow fluidic chambers each comprising an inlet fluidically connected to a reservoir of a biological solution, and an outlet;

a last row of laminar-flow fluidic chambers equal in number to the number of chambers of the first row, each fluidic chamber of the last row comprising:
  an inlet fluidically connected to an outlet of a chamber of the first row; and
  an outlet;

at least one reservoir for collecting the solution, fluidically connected to each outlet of the fluidic chambers of the second row;

at least one pump adapted to cause a sample of the biological solution to circulate in the fluidic chambers of the first row then of the last row;

the laminar-flow fluidic chambers each comprising a surface functionalized with molecules, at least some of which are able to form a bond with a receptor molecule borne by the target cells.

According to other embodiments:

the functionalized surfaces of the chambers of the first row may be provided with molecules capable of selectively binding to one or more cell population (s) of the sample other than the target cells, and the functionalized surfaces of the chambers of the last row and optionally of the intermediate row (s) may be provided with different types of molecules capable of selectively binding to a population or populations of target cells;

the fluidic chambers of the first row may be connected to the reservoir via a single liquid supply channel, consisting of as many channel segments as fluidic chambers, the segments of the supply channel being of different, and increasingly small, sections in the direction of circulation of the liquid, each segment being in fluidic communication with an inlet orifice of a fluidic chamber to cause the liquid to enter into each chamber;

each row may consist of a captor of particles of interest comprising:
  a cover comprising indentations to form the chambers, each indentation being in fluidic communication with a solution inlet orifice, and a solution outlet orifice;
  a slide mounted removably and in a leaktight manner under the cover, to form a bottom of the fluidic chambers, and comprising a surface, turned towards the cover, covered with a functionalized region facing each indentation;

the captor of particles of interest of the first row may comprise a cover provided with a liquid supply channel, intended to be connected to the reservoir, and consisting of as many channel segments as the cover comprises indentations, the segments of the supply channel being of different, and increasingly small, sections in the direction of circulation of the liquid, each segment being in fluidic communication with an inlet orifice to cause the liquid to circulate in the chambers;

the cover may be transparent;

the cover may be made of cyclic olefin copolymer;

the inlets of the fluidic chambers of each row, from the second row, may be connected to the outlets of the fluidic chambers of the preceding row via tubes less than 5 cm in length, preferably less than 3 cm, and having an internal diameter of between 0.5 and 1.4 millimeters;

the device may comprise, with reference to the position of use:
  an upper cover comprising a flat edge region and indentations to form the chambers of the first row, each indentation being in fluidic communication with a solution inlet orifice;
  at least two functionalized slides, each comprising a surface turned towards the cover covered with a functionalized region facing each indentation, and pierced with as many outlet orifices as there are functionalized regions;
  at least one spacer intended to be arranged in a leaktight manner between two functionalized slides, and comprising as many openings as the upper cover comprises indentations, each opening defining a chamber;
  a lower cover comprising as many outlets as the first cover comprises inlets;

the functionalized slides may be transparent to the wavelengths compatible with the instruments for analyzing the slides; and/or each slide may comprise a visual code which can be interpreted by a computer, the code comprising information relating to the molecules of the functionalized regions of the slide.

Another subject of the invention is a process for the selective, specific and simultaneous sorting of rare target cells in a biological sample at a concentration of between 1 and 10 cells per milliliter (ml) of sample, comprising the following steps:
  a) functionalizing slides with molecules capable of selectively binding to one or more cell population (s) over different regions of the slide, each intended to define a bottom of a fluidic chamber;
  b) fitting an above device according to the invention with the slides functionalized in this way;
  c) connecting the inlet of the chambers of the first row to a solution reservoir containing the target cells to sort, and the outlet of the chambers of the last row to a recovery reservoir;
  d) fluidically coupling the outlet of the chambers of one row to the inlet of the chambers of another row, until all the chambers are connected in series with one another, from one row to another;
  e) causing the biological sample to circulate in the chambers, from the first row to the last row, so as to bind target cells to the molecules capable of selectively binding to these cells;
  f) analyzing the functionalized surfaces of the slides containing the target cells bound in step e).

According to another embodiment, the step a) may consist in:
  a1) functionalizing the regions of the slide of the first row with molecules capable of selectively binding to one or more of the most numerous cell population (s) in the sample considered other than the target cells;
  a2) functionalizing the regions of the slide of the following row(s) with different types of molecules capable of selectively binding to a population or populations of target cells, each functionalized region comprising a single type of said molecules.

The device and the process according to the invention have the advantage of enabling selective, specific and simultaneous sorting, by virtue of the combination of positive selection and negative selection of the cells and their heterogeneous sub-populations, for example in the peripheral blood and in the bone marrow.

The versatility of the process and of the device according to the invention enables grafting of a broad spectrum of various antibodies enabling, in a single step, positive selection and negative selection of targeted cells on each row, constituting a mesofluidic immunosensor provided with N independent laminar-flow chambers (N being an integer advantageously between 4 and 6 inclusive), arranged in parallel, for example on a microscope slide functionalized with silanes.

The process and the device according to the invention make it possible to respond to a medical issue; that of detecting sub-populations of rare cells in oncology, in predictive medicine, in regenerative medicine, etc.

They make it possible to selectively detect, in each laminar-flow chamber, one to ten rare cells characteristic of a sub-population, in one milliliter (ml) of blood containing $10 \times 10^9$ blood cells.

The applications are multiple: solid tumor oncology, malignant hemopathies, etc.

A major benefit of the present invention is that it makes it possible to respond to medical requirements in the case of triple negative breast cancer, the circulating tumor cells of which do not express the surface antigen EpCAM.

Other characteristics of the invention will be given in the detailed description below, made with reference to the appended drawings, in which, respectively.

Figure 1:
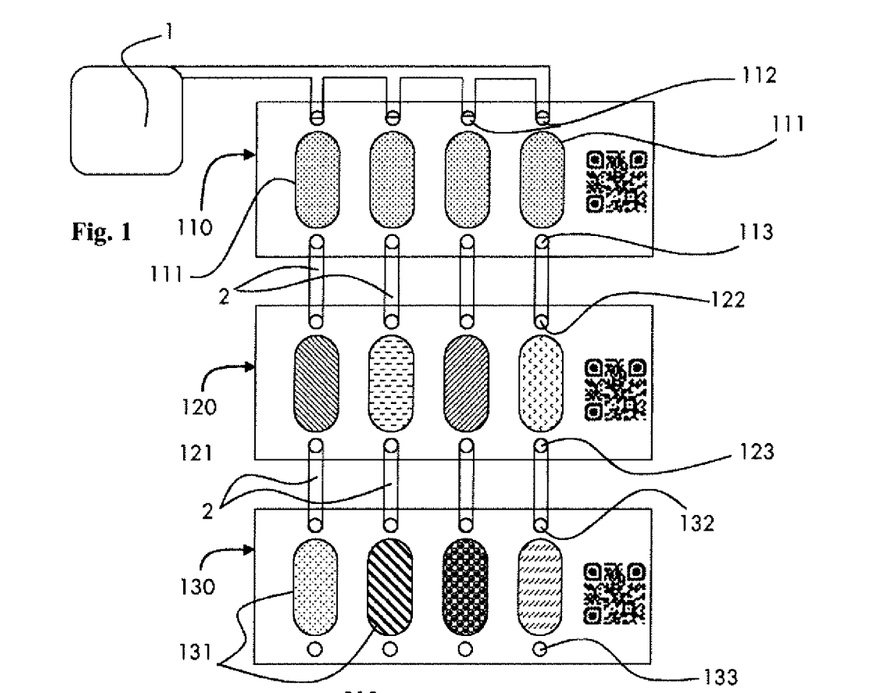
FIG. 1 represents a schematic plan view of a first embodiment of a device for sorting target cells according to the invention with three stages.

FIG. 1 illustrates a sorting device 100 according to the invention, comprising a first row 110 of fluidic chambers 111 each provided with an inlet 112 fluidically connected to a single reservoir 1 of a biological solution, and an outlet 113. In this exemplary embodiment, this first row comprises four fluidic chambers 111.

Advantageously, the fluidic chambers 111 of the first row are connected to the reservoir via a single liquid supply channel, consisting of as many channel segments as fluidic chambers 111, the segments of the supply channel being of different, and increasingly small, sections in the direction of circulation of the liquid, each segment being in fluidic communication with an inlet orifice of a fluidic chamber 111 to cause the liquid to enter into each chamber. As will be described in relation to FIGS. 3 and 19, this channel is advantageously borne by a rigid cover.

The device 100 also comprises a second row 120 of fluidic chambers 121 equal in number to the number of chambers 111 of the first row 110. Each fluidic chamber of the second row comprises an inlet fluidically connected to an outlet of a chamber of the first row, and an outlet. In other words, if the chambers of the same row are mounted in parallel, meaning that they are not in communication with one another, the chambers of two successive rows are mounted in series, meaning that they are in fluidic communication in the direction of circulation of the sample.

The device 100 also comprises a last row 130 of fluidic chambers 131 equal in number to the number of chambers 111 of the first row 110. Each fluidic chamber of the last row comprises an inlet 132 fluidically connected to an outlet of a chamber of the first row. In this embodiment, this fluidic connection is indirect and is achieved via the chambers 121 of the second row.

In an alternative embodiment, in which there were no intermediate row (in this case the second row), the fluidic connection between the last row and the first row would be direct.

The fluidic chambers 131 of the last row also comprise an outlet 133. The outlets 133 of the last row are fluidically connected to a collection reservoir, not illustrated in the figure.

The inlets of the fluidic chambers of each row, starting from the second row, are connected to the outlets of the fluidic chambers of the preceding row via tubes 2 less than 5 cm in length, preferably less than 3 cm, and having an internal diameter of between 0.5 and 1.4 millimeters.

These dimensions reduce the dead volume of sample (portion of the sample remaining in the tubes), which makes it possible to limit the risks of the rare cells remaining in the tubes and not being collected by the fluidic chambers.

The liquid sample circulates in the device from the reservoir of biological solution 1 towards the collection reservoir, passing through the three rows of fluidic chambers. This circulation is enabled by a pump (not illustrated). This pump may be configured to push and/or to suck the liquid through the rows of fluidic chambers.

In other words, a flow rate is established in each chamber by a pump applied upstream and/or downstream of the fluidic chambers. According to a preferred embodiment, the pump is a multi-channel peristaltic pump.

The fluidic chambers 111, 121, 131 each comprise a surface functionalized with molecules, at least some of which are able to form a bond with a receptor molecule borne by the target cells. These may advantageously be antibodies grafted to surface-binding molecules such as silanes.

According to the invention, the chambers have mesofluidic-scale dimensions and provide a laminar flow (that is to say a flow without turbulence).

The mesofluidic scale relates to devices, the dimensions and configurations of which vary from a few millimeters to one or more centimeters. These devices differ from microfluidic devices, at least one of the characteristic dimensions of which is of the order of a micrometer.

The choice of this mesofluidic scale, by virtue of the laminar-flow chambers, makes it possible to reduce rheological phenomena which are as yet poorly controlled in microfluidics. A laminar flow imposes fewer stresses on the cells which may be fragile, and enables uniform coverage of the functionalized surface by the sample, gentle immobilization of the cells, and an increase in the cell capture efficiency.

Figure 2:
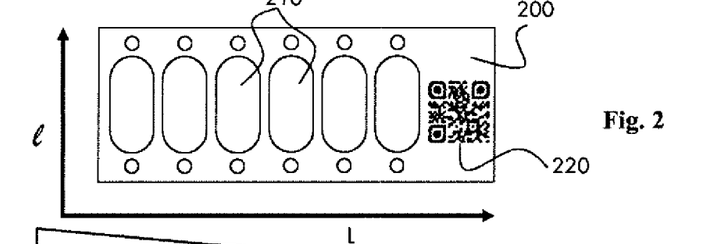
FIG. 2 represents a schematic plan view of a standard microscope slide with six functionalized regions.

According to a preferred embodiment illustrated in FIG. 2, the functionalized surface 210 of the fluidic chambers is borne by a glass slide 200, such as a standard microscope slide with the dimensions L×l equal to 76×25 mm (3"×1").

With a slide 200 of these dimensions, four to six functionalized regions 210 are preferably produced (corresponding to four to six fluidic chambers), having an oblong shape circumscribed by a rectangle 16 mm long and 6 mm wide.

The arrangement of the chambers is preferably such that a free space is arranged at one end of the glass slide, in order to place a visual code 220 there which can be interpreted by a computer, such as a barcode or a Flash Code.

Generally, the functionalized slides are advantageously transparent to the wavelengths compatible with instruments for analyzing the slides. If the analytical instrument is an optical microscope, then the slides are advantageously made of glass or a polymer transparent to the wavelengths visible to a human.

Figures 3, 4:
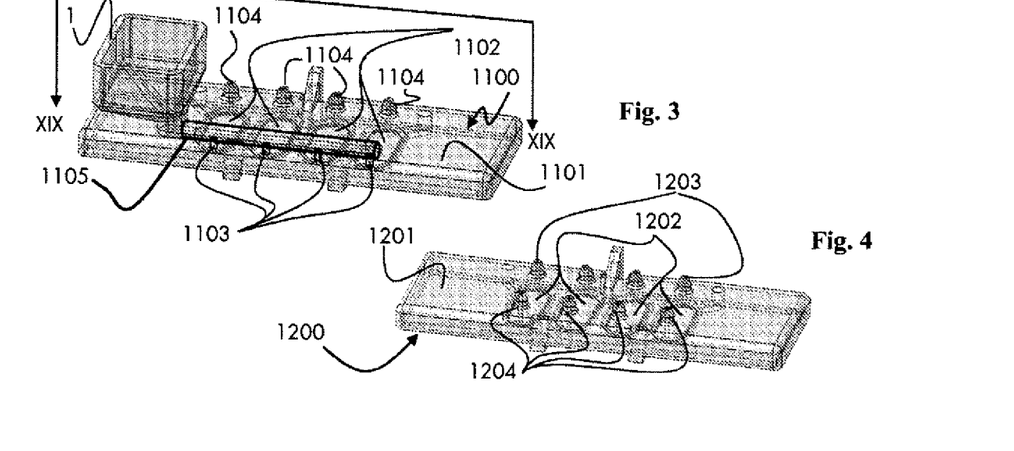
FIG. 3 represents a schematic perspective view of an exemplary embodiment of a first-row captor of particles of interest.
FIG. 4 represents a schematic perspective view of an exemplary embodiment of a last-row or intermediate-row captor of particles of interest.

According to a preferred embodiment illustrated for example in FIGS. 3 and 4, each row 110, 120, 130 consists of a captor of particles of interest 1100, 1200 comprising a cover 1101, 1201, comprising indentations 1102, 1202 to form the chambers, each indentation being in fluidic communication with a solution inlet orifice 1103, 1203, and a solution outlet orifice 1104, 1204.

The indentations have a thickness e (see FIG. 4) determining the height of each chamber. This thickness e is preferably chosen to be equal to approximately 0.5 mm. With a standard size microscope slide 2 having four chambers 16 mm long and 6 mm wide, this gives a captor of particles of interest having laminar-flow chambers each of 48 mm$^3$.

The small volume of each of these chambers nonetheless enables a laminar flow and a reaction of the particles of interest with relatively little liquid.

A slide is mounted removably and in a leaktight manner under the cover 1101, 1201, to form a bottom of the fluidic chambers, the slide comprising a surface turned towards the cover and covered with a functionalized region facing each indentation.

The captor of particles of interest of FIG. 3 is a captor suitable for being placed in the first row. It directly incorporates a solution reservoir 1. It comprises a cover 1101 provided with a liquid supply channel 1105 connected to the reservoir 1, and consisting of as many channel segments as the cover comprises indentations 1102. The segments of the supply channel are of different, and increasingly small, sections in the direction of circulation of the liquid, each segment being in fluidic communication with an inlet orifice 1103 to cause the liquid to circulate in the chambers. Such an arrangement enables uniform diffusion and distribution of the liquid sample in each of the fluidic chambers of the first row.

Figure 19:
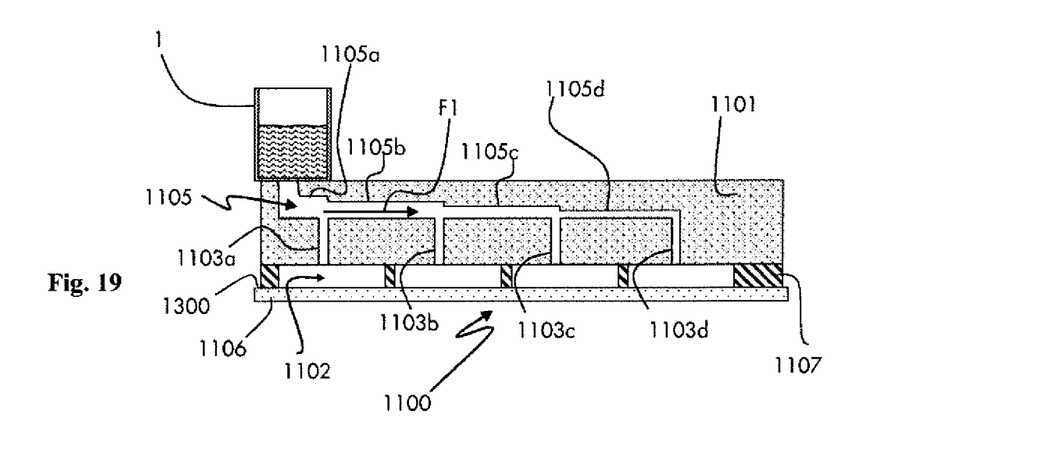
FIG. 19 represents a schematic sectional view of the embodiment of a device for sorting target cells of FIG. 3.

A sectional view of the exemplary embodiment of FIG. 3 is illustrated in FIG. 19.

The particle captor 1100 comprises a slide 1106, preferably made of glass or silicon, one face of which is functionalized by means of recognition molecules adapted to the particles which it is desired to capture in the liquid. Advantageously, according to the invention, the particles captured in row 1 are not the particles of interest but are other particles, the row 1 at least serving to capture uninteresting particles so as to "filter" the sample, in order to purify it, after a fashion, and enable the capture of the particles of interest in the last row (or even starting from a preceding row, depending on the number of rows).

A seal 1107 is arranged on the slide 1106. It is provided with four openings each delimiting the contour of one laminar-flow chamber 1102.

The cover 1101 is arranged above the seal 1107 and comprises a supply channel 1105 for supplying each chamber 1102 with liquid, and outlet ducts 1104 (not illustrated in FIG. 19) for the liquid from each of the chambers.

The supply channel 1105 is provided with as many channel segments as the seal comprises openings. In the example illustrated, the supply channel 1105 comprises four channel segments 1105a, 1105b, 1105c and 1105d.

The supply channel 1105 is provided with means for accelerating the liquid along the channel. In the exemplary embodiment illustrated in FIG. 19, the acceleration means are formed by the four segments 1105a, 1105b, 1105c, and 1105d of the supply channel each having different sections, the sections being increasingly small in the direction of circulation of the liquid, following the arrow F1. These different sections constitute a means for accelerating the liquid, making it possible to keep the speed of the liquid along the supply channel 1105 substantially constant, which provides uniform distribution and circulation of the particles of interest in each chamber.

In the example of FIG. 19, the supply channel comprises a means for accelerating the fluid such that the mean speeds of the fluid, upstream and downstream of a duct for admission of the liquid into a given chamber, remain substantially constant. This enables uniform distribution of the particles between the chambers and within the same chamber, and ensures reproducibility of experimental conditions between the different chambers of the same mesofluidic device.

Each admission duct is preferably arranged vertically aligned with each section narrowing.

Thus, for a mesofluidic device according to the invention containing n chambers, which must have a flow rate q in each duct for admission of liquid into a chamber, having an initial section S upstream of the chambers, the sections are reduced by 1 $n^{th}$ of S at each channel segment.

For example, for the mesofluidic device containing four chambers in FIG. 19, the supply channel 1105 has a first segment 1105a with a section S1, a second segment 1105b with a section S2=¾ of S1, a third segment 1105c with a section S3=½ of S1, and a fourth segment 1105d with a section S4=¼ of S1.

By virtue of this particular change in section, the speed of the fluid in each segment remains substantially constant.

The cover is advantageously transparent, and preferably consists of cyclic olefin copolymer, such as TOPAS® COC sold by TOPAS Advanced Polymers.

The captor of particles of interest of FIG. 4 is a captor suitable for being placed starting from the second row, up to the last row.

Figure 5:
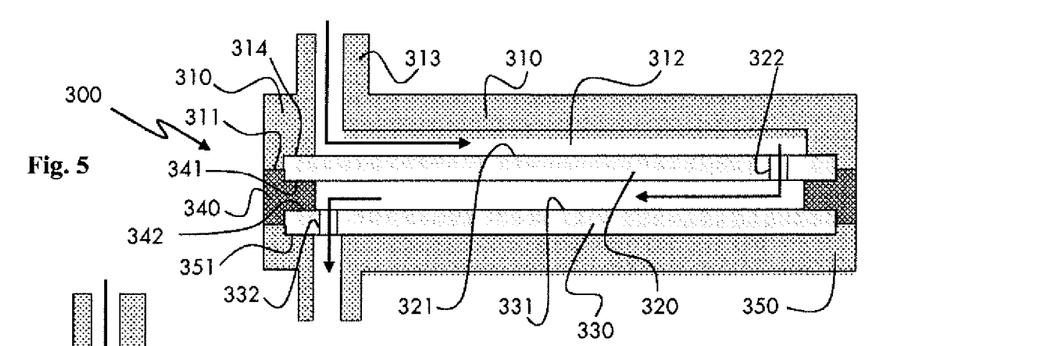
FIG. 5 represents a schematic sectional view of a second embodiment of a device for sorting target cells according to the invention with two stages.

FIG. 5 illustrates a second embodiment of a sorting device according to the invention, enabling stacking of the rows of fluidic chambers and a reduction in the length of the fluidic connections between the different rows.

The device 300 comprises, with reference to the position of use:
an upper cover 310 comprising a flat edge region 311 and indentations 312 to form the chambers of the first row, each indentation 312 being in fluidic communication with a solution inlet orifice 313;
two functionalized slides 320-330, each comprising a surface 321-331 turned towards the cover covered with a functionalized region facing each indentation, and pierced with as many outlet orifices 322-332 as there are functionalized regions. These orifices enable the fluidic connection between the different rows of chambers and serve the same function as the tubes 2 from the embodiment of FIG. 1;
a spacer 340 intended to be arranged in a leaktight manner between the two functionalized slides 320-330, and comprising as many openings as the upper cover comprises indentations, each opening defining a chamber; and
a lower cover 350 comprising as many outlets 351 as the first cover 310 comprises inlets 313.

The indentations 312 and the spacer 340 have a thickness e determining the height of each chamber. This thickness e is preferably chosen to be equal to approximately 0.5 mm.

Such a device takes up a relatively small amount of space and is easy to use.

Figure 6:
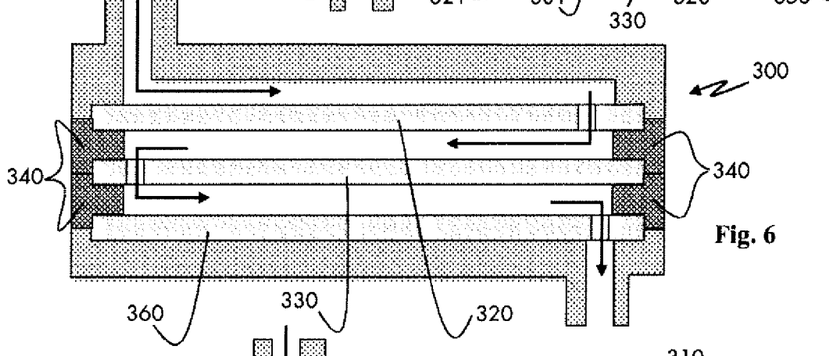
FIG. 6 represents a schematic sectional view of the embodiment of a device for sorting target cells of FIG. 5, with an additional stage.

In addition, it is multipurpose since a stage of fluidic chambers can be readily added, as is illustrated in FIG. 6. In this figure, the device 300 comprises an additional spacer 340, and an additional functionalized slide 360.

In the embodiments of FIGS. 5 and 6, the upper cover 310 and lower cover 350, and also the spacers 340, comprise shoulders 314, 351, 341 and 342, respectively, making it possible to laterally hold the slides 320, 330 and 360 firmly.

A holding means may be provided to hold the assembly in position such that the spaces between the slides, the spacers and the covers are leaktight.

Figure 7:
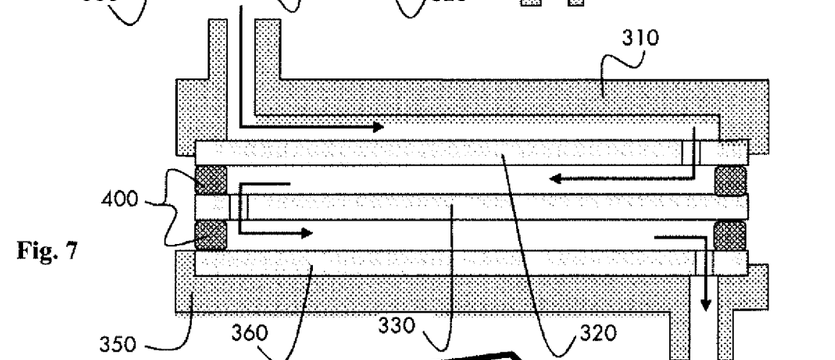
FIG. 7 represents a schematic sectional view of a third embodiment of a device for sorting target cells according to the invention with three stages.
Figure 18:
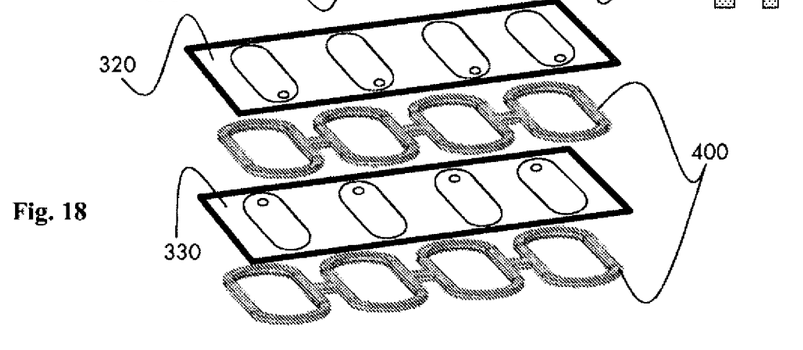
FIG. 18 represents a schematic partial perspective view of the embodiment of a device for sorting target cells of FIG. 7.

A simpler embodiment is illustrated in FIGS. 7 and 18, in which the spacers are seals 400 arranged between the functionalized regions of the slides to define the fluidic chambers.

Of course, seal is understood in the broad sense. It may consist of several independent loops, that is to say which are not connected to one another, but which each delimit the contour of a laminar-flow chamber. However, it is more practical for the seal to consist of a single part comprising several openings, that is to say forming several loops which are connected to one another. This second embodiment is illustrated in FIG. 18. The covers 310 and 350 are not illustrated in this FIG. 18.

In order to implement these embodiments, the functionalized slides may advantageously be made of polymer to enable piercing of the orifices 322-332. For example, the polymer may be a "functionalized silicone" polymer (PDMS type=functionalized polydimethylsiloxane), PMMA, etc., keeping GPTS as coupling agent for proteins (antibodies, etc.).

A device according to the invention makes it possible to carry out a process for the selective, specific and simultaneous sorting of target cells in a biological sample, comprising the following steps:
a) functionalizing slides with antibodies over different regions of the slide, each intended to define a bottom of a fluidic chamber;
b) fitting a device according to the invention with the slides functionalized in this way;
c) connecting the inlet of the chambers of the first row to a solution reservoir containing the target cells to sort, and the outlet of the chambers of the last row to a recovery reservoir;
d) fluidically coupling the outlet of the chambers of one row to the inlet of the chambers of another row, until all the chambers are connected in series with one another, from one row to another;
e) causing the biological sample to circulate in the chambers, from the first row to the last row;
f) analyzing the functionalized surfaces of the slides containing the rare target cells.

Advantageously, step a) consists in:
a1) functionalizing the regions of the slide of the first row with molecules capable of selectively binding to one or more of the most numerous cell population(s) in the sample considered other than the target cells;
a2) functionalizing the regions of the slide of the following row (s) with different types of molecules capable of selectively binding to a population or populations of target cells, each functionalized region comprising a single type of said molecules.

A device is thus obtained, in which:
the functionalized surfaces of the chambers of the first row are provided with molecules capable of selectively binding to one or more cell population (s) of the sample other than the target cells;
the functionalized surfaces of the chambers of the last row and optionally of the intermediate row (s) are provided with different types of molecules capable of selectively binding to a population or populations of target cells.

In this way, negative selection is carried out in the first row, that is to say selection of cells other than those which it is eventually desired to sort. For example, if a blood sample is in question, the first row may advantageously be functionalized with antibodies having an affinity with leukocytes, in order to remove this type of cell from the sample.

Positive selection may be carried out for example in the second row, by functionalizing the N fluidic chambers with antibodies having an affinity for different types of rare cells to be trapped.

More generally, negative selection according to the invention makes it possible to "clean" the sample before carrying out positive selection.

If several types of cells must be eliminated by negative selection, it is possible to provide adapted functionalization of the p first rows. The following rows are then functionalized to carry out positive selection of the rare cells to be trapped.

By virtue of the device according to the invention, negative and positive selection may be carried out in a single operation, that is to say in a single passage of the sample through the device.

Several examples of applications are described below:

A surface consisting of a self-assembled monomolecular layer of short chain silanes with epoxide end groups, 3-glycidoxypropyltrimethoxysilane (GPTS), is used to functionalize the standard microscope slides. The surface functionalized with the GPTS is perfectly hydrophilic and retains 1) its properties of physical stability under shearing and at temperature, 2) its properties of chemical resistance to UV radiation and to hydrolysis at pH 7.4, and 3) the preservation of the biological properties of the protein ligands grafted to the GPTS chains. The antibodies are coupled directly onto the self-assembled monomolecular layer of GPTS silanes. The natural properties of the specific antibodies are entirely preserved on the monolayer of GPTS silanes.

EXAMPLE 1: GRAFTING OF ANTIBODIES FOR NEGATIVE AND POSITIVE Selection

The leukocytes are eliminated in negative selection by capture in row 1 on the microscope slide by means of an anti-CD45 antibody grafted to the surface functionalized by GPTS (Multiplex I distributor with one reservoir, chamber 1 to chamber 4: FIG. 3, table 1).

TABLE 1

Level 1, Multiplex I distributors with one reservoir

| Bases + GPTS | Chamber 1 | Chamber 2 | Chamber 3 | Chamber 4 |
| --- | --- | --- | --- | --- |
| Row 1-antibody | Anti-CD45 | Anti-CD45 | Anti-CD45 | Anti-CD45 |

In selective, specific and simultaneous positive selection of the rare sub-populations, each laminar-flow chamber in row 2 composing the captor of particles of interest is grafted by means of specific antibodies according to each sub-population as follows (FIG. 4, table 2):
Chamber 1) the anti-EpCAM antibody for selectively and specifically selecting cells of epithelial origin (CTC),
Chamber 2) the anti-N-cadherin antibody for selectively and specifically selecting non-epithelial mesenchymal cells,
Chamber 3) the anti-CD133 antibody for selectively and specifically selecting cancer stem cells (CSC), for example in colon cancer,
Chamber 4) and the anti-CD44 antibody for selectively and specifically selecting cancer stem cells (CSC), for example in colon cancer.

TABLE 2

3-Level combination of the captors of particles of interest with and without reservoir

| Bases + GPTS | Chamber 1 | Chamber 2 | Chamber 3 | Chamber 4 |
| --- | --- | --- | --- | --- |
| Row 1-captors of particles of interest with reservoir | Anti-CD45 | Anti-CD45 | Anti-CD45 | Anti-CD45 |
| Row 2-captors of particles of interest without reservoir | Anti-EpCAM | Anti-N-cadherin | Anti-CD133 | Anti-CD44 |
| Row 3-captors of particles of interest without reservoir | Anti-EpCAM | Anti-N-cadherin | Anti-CD133 | Anti-CD44 |

The same selective, specific and simultaneous positive selection of the same sub-populations may be repeated in row 3, identical to row 2, to reinforce the cell capture statistics (table 2).

Alternatively, in row 3, the grafting of the antibodies in the captor of particles of interest may be inverted as follows (table 3):
Chamber 1) the anti-N-cadherin antibody for selectively and specifically selecting non-epithelial mesenchymal cells,
Chamber 2) the anti-EpCAM antibody for selectively and specifically selecting cells of epithelial origin (CTC),
Chamber 3) the anti-CD44 antibody for selectively and specifically selecting cancer stem cells (CSC), for example in colon cancer,
Chamber 4) and the anti-CD133 antibody for selectively and specifically selecting cancer stem cells (CSC), for example in colon cancer.

TABLE 3

3-Level combination of the captors of particles of interest with and without reservoir

| Bases + GPTS | Chamber 1 | Chamber 2 | Chamber 3 | Chamber 4 |
| --- | --- | --- | --- | --- |
| Row 1-captors of particles of interest with reservoir | Anti-CD45 | Anti-CD45 | Anti-CD45 | Anti-CD45 |
| Row 2-captors of particles of interest without reservoir | Anti-EpCAM | Anti-N-cadherin | Anti-CD133 | Anti-CD44 |
| Row 3-captors of particles of interest without reservoir | Anti-N-cadherin | Anti-EpCAM | Anti-CD44 | Anti-CD133 |

Variant

There is also a benefit to the detection of rare, non-hematopoietic sub-populations in the peripheral blood. Circulating endothelial cells (CEC) are biomarkers of vascular damage in inflammatory, immune, infectious, neoplastic and cardiovascular pathological conditions.

An example of a process for detecting sub-populations of rare cells comprising cells of epithelial origin (CTC), non-epithelial mesenchymal cells, cancer stem cells (CSC) and circulating endothelial cells (CEC). The respective grafted antibodies are: anti-EpCAM for the sub-population of tumor cells of epithelial origin (CTC), anti-N-cadherin for the sub-population of mesenchymal cells, anti-CD133 for the sub-population of cancer stem cells (CSC) and anti-CD146 for the sub-population of non-hematopoietic cells (CEC) (tables 4 and 5).

TABLE 4

3-Level combination of the captors of particles of interest with and without reservoir

| Bases + GPTS | Chamber 1 | Chamber 2 | Chamber 3 | Chamber 4 |
| --- | --- | --- | --- | --- |
| Row 1-captors of particles of interest with reservoir | Anti-CD45 | Anti-CD45 | Anti-CD45 | Anti-CD45 |
| Row 2-captors of particles of interest without reservoir | Anti-EpCAM | Anti-N-cadherin | Anti-CD133 | Anti-CD146 |
| Row 3-captors of particles of interest without reservoir | Anti-EpCAM | Anti-N-cadherin | Anti-CD133 | Anti-CD146 | or

TABLE 5

3-Level combination of the captors of particles of interest with and without reservoir

| Bases + GPTS | Chamber 1 | Chamber 2 | Chamber 3 | Chamber 4 |
|---|---|---|---|---|
| Row 1-captors of particles of interest with reservoir | Anti-CD45 | Anti-CD45 | Anti-CD45 | Anti-CD45 |
| Row 2-captors of particles of interest without reservoir | Anti-EpCAM | Anti-N-cadherin | Anti-CD133 | Anti-CD146 |
| Row 3-captors of particles of interest without reservoir | Anti-N-cadherin | Anti-EpCAM | Anti-CD146 | Anti-CD133 |

This series mounting of the captors of particles of interest with one reservoir (row 1; see FIG. 3), and the captors of particles of interest without reservoir (see FIG. 4) makes it possible, in a manner well defined by the user, to target four sub-populations of interest selectively, specifically and simultaneously. The device according to the invention makes it possible to overcome the inadequacies of the known detection methods using a single anti-EpCAM antibody.

Indeed, conventional detection with a single anti-EpCAM antibody is absolutely unable to detect, at the same time, non-epithelial mesenchymal cells, or cancer stem cells, or non-hematopoietic endothelial cells.

EXAMPLE 2: VISUALIZATION OF CELL MARKERS BY IMMUNOFLUORESCENCE

Two examples of selective, specific and simultaneous detection: 1) a sub-population of CTC of epithelial origin, and 2) a sub-population of non-hematopoietic cells CEC (circulating endothelial cells) by protein cell markers in metastatic colon and prostate cancers.

1. Negative Selection: Leukocyte Filtration

The anti-leukocyte antibody anti-CD 45 targets the majority of the leukocytes in the blood.

Figure 8:
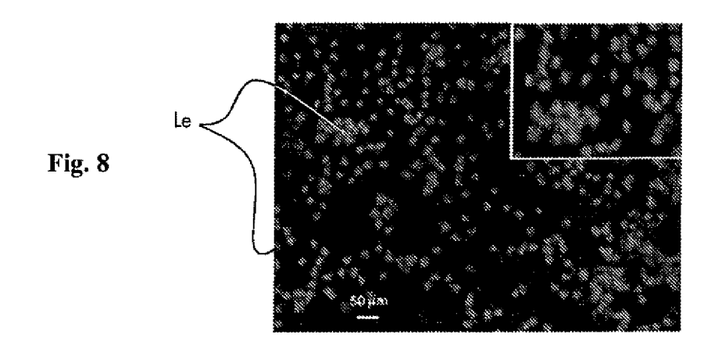
FIG. 8 represents a photograph of a visualization of cell markers by immunofluorescence of a negative selection of leukocytes.

FIG. 8 visualizes the high leukocyte population i.e. The leukocytes are stained with the nuclear stain DAPI.

2. Positive Selection

A. CTC of Epithelial Origin

The antigen EpCAM is a cell adhesion molecule expressed on the surface of the tumor cell of epithelial origin. Grafting the anti-EpCAM antibody onto a standard microscope slide functionalized with GPTS (3-glycidoxypropyltrimethoxysilane), in a phosphate buffer (PBS), pH 7.4, containing 0.5% trehalose (Sigma), makes it possible to target identification of CTCs of epithelial origin. The CTCs are then identified by a cell marker expressing cytokeratin, the antibody anti-pan cytokeratin, in a phosphate buffer (PBS), containing 0.1% bovine serum albumin (BSA). Characterization is carried out by immunofluorescence to confirm the epithelial origin of the cell detected.

Figure 9:
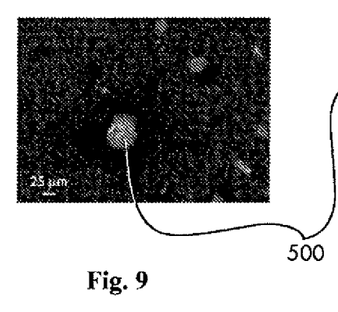
FIGS. 9 and 10 represent photographs of a visualization of cell markers by immunofluorescence of a positive selection of CTC cells.
Figure 10:
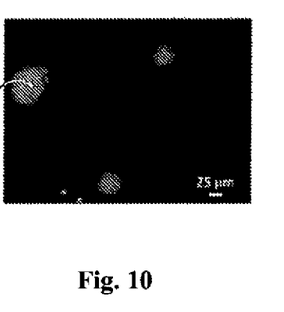

FIGS. 9 and 10 show a CTC 500, captured by the anti-EpCAM antibody (green fluorescence), originating either from a metastatic colon cancer (FIG. 9) or from a metastatic prostate cancer (FIG. 10). The nuclear stain is DAPI (blue).

B. Non-Hematopoietic Cells: Circulating Endothelial Cell (CEC)

MCAM is a glycoprotein expressed on the surface of the endothelial cell. Grafting the anti-MCAM antibody (anti-CD146) onto a standard microscope slide functionalized with GPTS (3-glycidoxypropyltrimethoxysilane), in a phosphate buffer (PBS), pH 7.4, containing 0.5% trehalose (Sigma), makes it possible to target their identification and capture. The CECs are then identified by the anti-CD144 antibody directed against VE (vascular endothelial)-cadherin, in a phosphate buffer (PBS), containing 0.1% bovine serum albumin (BSA). Characterization is carried out by immunofluorescence to confirm the endothelial cell.

Figure 11:
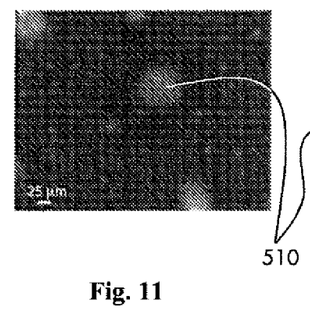
FIGS. 11 and 12 represent photographs of a visualization of cell markers by immunofluorescence of a positive selection of CEC cells.
Figure 12:
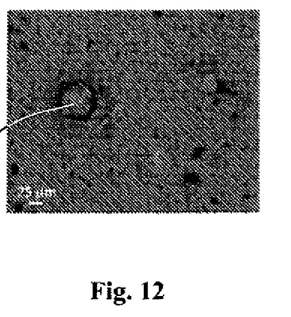

FIGS. 11 and 12 show a CEC 510 originating from a metastatic colon cancer (FIG. 11) and a CEC from a metastatic prostate cancer (FIG. 12). The CECs are characterized by immunofluorescence by the anti-CD144 antibody (purple fluorescence). The nuclear stain is DAPI (blue).

A non-exhaustive list of the markers which may be used to target the sub-populations of cells of epithelial and non-epithelial origin for their characterization and identification is given below:

| Cell type | Marker(s) used to isolate sub-populations |
|---|---|
| Epithelial | EpCAM, BerEP4, MUC 1, |
| Mesenchymal | N-cadherin, cadherin 11 |
| Endothelial | MCAM (CD146), VE-cadherin (CD144) |
| Leukocyte | CD45 |
| T lymphocyte | CD3 |
| B lymphocyte | CD20 |
| Hematopoietic stem cell | CD34 |
| Mesenchymal stem cell | CD44, CD45, CD90, CD150, CD299 |
| Tumor cell (breast cancer, prostate cancer) | HER2 |

A list of the markers which may be used to target the sub-populations of cancer stem cells (CSC) for their characterization and identification is given below:

| Tumor type | Marker(s) used to isolate CSC |
|---|---|
| Malignant hemopathies | CD34+, CD38− |
| Colon | CD133+, CD44+, Lin− |
| Breast | CD44+, CD24−/low |
| Melanoma | ABCB5 transporter |
| Prostate | CD44+ , CD133+, α2β1 |
| Pancreas | CD44+ , CD24, CD133+ |
| Glioblastoma | CD133+ |
| Liver | CD133+, CD44+ , CD90+ |
| Lung | CD133+ |
| UADT | CD44+ |

Another major and user-friendly technical advantage of the device according to the invention relates to the unique development of the characterization of cells of interest accompanied by a series of successive molecular analyses.

The flow of molecular characterization consists of a multi-step identification process, on the same glass slide and the same cell, 1) by means of a fluorescent protein marker (antibody), 2) by analysis of genomic changes (gene amplifications, deletions, and rearrangements) by fluorescence in situ hybridization (FISH) by means of specific DNA probes, 3) in situ characterization of mRNAs by specific RNA probes and of micro-RNAs (miRNAs) by nanoprobes.

EXAMPLE 3: VISUALIZATION OF GENOMIC CHANGES IN SUB-POPULATIONS OF CTCS BY FLUORESCENCE IN SITU HYBRIDIZATION (FISH): GENE AMPLIFICATIONS, DELETIONS AND REARRANGEMENTS, BY MEANS OF SPECIFIC DNA PROBES

The added value of the standard microscope slide functionalized for detection of sub-populations of CTCs of epithelial and non-epithelial origin is its remarkable capacity to be able to undergo multiple successive treatments, such as:

1) labeling of cells of interest by fluorescent protein cell markers, and identification of said labeling under the microscope, 2) a specific treatment is applied to eliminate the fluorescent background, then a reconditioning of the cells of interest detected by the labeling of the nuclei by nucleic probes by means of fluorescence in situ hybridization (FISH) to identify their genomic changes.

Figure 13:
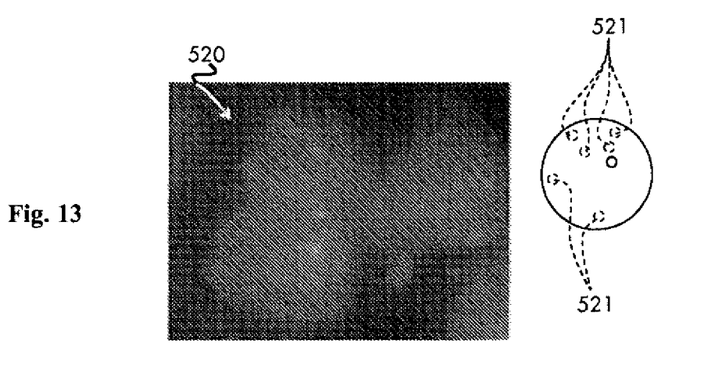
FIGS. 13 to 15 represent photographs of a visualization of genomic changes in sub-populations of CTC cells.

FIG. 13 shows the nucleus 520 of a CTC of epithelial origin of a metastatic colon cancer, showing a gene amplification (dashed circles 521) revealed by means of a probe targeting the gene EGFR (Kreatech, Holland).

Figures 14, 15:
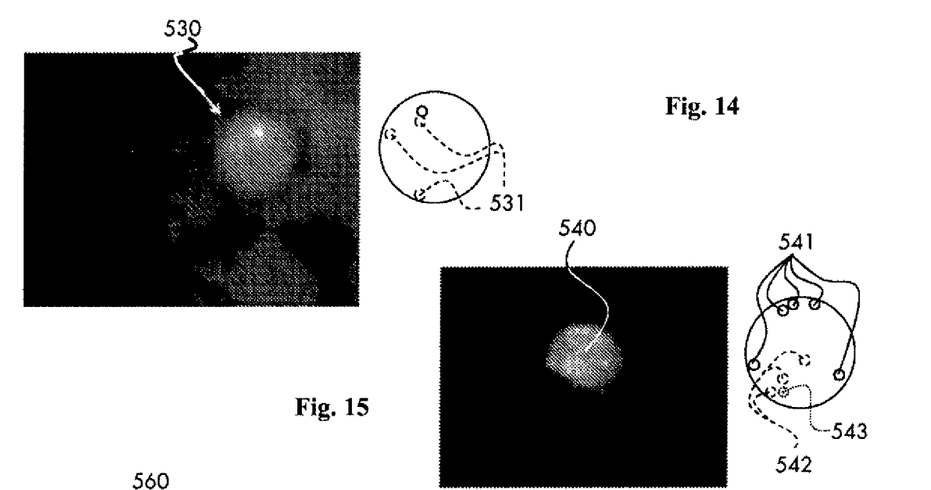

FIG. 14 shows the nucleus of a CTC 530 of epithelial origin of a metastatic prostate cancer, showing a gene amplification (dashed circles 531) revealed by means of a probe targeting the gene PTEN (Kreatech, Holland).

FIG. 15 shows the nucleus of a CTC 540 of epithelial origin of a metastatic prostate cancer, showing a gene amplification (solid-line circles 541, dashed circles 542 and greyed-out circle 543) revealed by means of a probe targeting the gene fusion TMPRSS2-ERG (Kreatech, Holland).

The device according to the invention may also be used for two particularly advantageous applications:

EXAMPLE 4: ANALYSIS OF MRNAS AND MIRNAS IN LIVING CELLS

The capture of living, single cells by the device according to the invention and in particular the captors of particles of interest with and without reservoir, is an asset for simultaneous multiplex analysis of mRNA by means of nanoparticles functionalized with multiple nucleotide sequences and operating as direct hybridization probes (Smart Flares, Merck-Millipore), each probe being coupled to a chromophore.

In addition, the second asset is its application with the intention of analyzing miRNAs in a living, single cell (Smart Flares, Merck-Millipore). miRNAs are biomarkers of tumor progression.

They are novel analytical tools for supplementing early diagnosis, anticipating disease progression, identifying high-risk patients, predicting recurrence after treatment and monitoring the patient's response to treatment.

Figure 16:
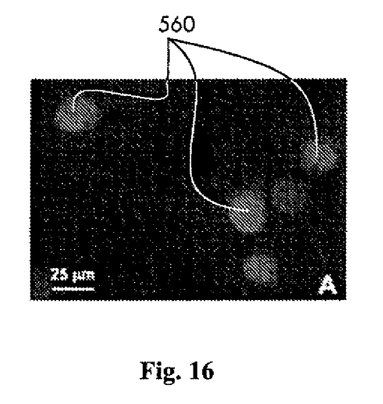
FIG. 16 represents a photograph of an example of labeling of living MCF-7 breast cancer cells by a control probe for endocytosis, with a view to mRNA and miRNA labeling.

FIG. 16 illustrates an example of labeling of living MCF-7 breast cancer cells 560 by a control probe for endocytosis, with a view to mRNA and miRNA labeling (Smart Flares, Merck-Millipore). The MCF-7 breast cancer cells 560 are captured on a microscope slide functionalized with GPTS and grafted with the anti-EpCAM antibody. They are then labeled with a control probe for endocytosis of the nanoparticles and incubated at 37° C. under 5% $CO_2$ for 12 hours.

EXAMPLE 5: CELL CULTURE WITH THE CAPTOR OF PARTICLES OF INTEREST WITHOUT RESERVOIR

Figure 17:
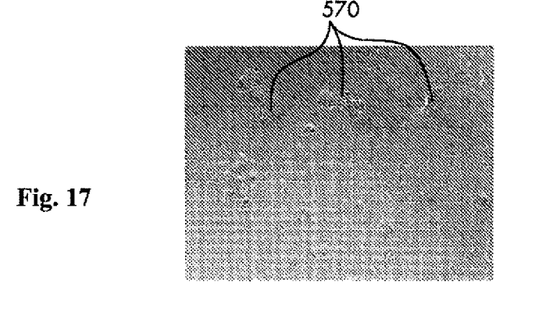
FIG. 17 represents a photograph following 5 days of cell culture with the captor of particles of interest without reservoir according to the invention.

For culturing cells, the captor of particles of interest without reservoir and its GPTS-functionalized slide are sterilized in absolute ethanol for 3 minutes. After drying, the base of each chamber is grafted with the anti-EpCAM antibody for the capture of MCF-7 breast cancer cells. The captor of particles of interest without reservoir is then placed in a sterile Petri dish and incubated in an incubator at 37° C. and 5% $CO_2$ for 5 days. After 5 days, clusters 570 of MCF-7 breast cancer cells have developed (FIG. 17).

In summary, the great advantage of the process and the device according to the invention is their capacity for selective, specific and simultaneous sorting of all the heterogeneous sub-populations of circulating rare cells, regardless of the disease stage (localized or metastatic cancer). In addition, the user-friendly nature of the device according to the invention enables 1) grafting of antibodies targeting each sub-population of cells of interest, 2) high-performance molecular analyses of the cells of interest by virtue of the glass slide support, which withstands multiple experimental operations, is user-friendly and inexpensive compared to Si supports.

The invention claimed is:

1. A mesofluidic device (100) for selective, specific and simultaneous sorting of rare target cells in a biological sample at a concentration of between 1 and 10 cells per milliliter of sample, comprising:
 a first row (110) of at least two fluidic chambers (111), each fluidic chamber comprising an inlet (112) fluidically connected to a reservoir (1) of a biological solution, and an outlet (113);
 a last row (130) of fluidic chambers (131) equal in number to the number of the fluidic chambers (111) of the first row (110), each fluidic chamber (131) of the last row (130) comprising:
  an inlet (132) fluidically connected to an outlet (113) of a corresponding fluidic chamber (111) of the first row (110); and
  an outlet (133);
 at least one reservoir for collecting the solution, fluidically connected to each outlet (133) of the fluidic chambers of the last row;
 at least one pump adapted to cause a sample of the biological solution to circulate in the fluidic chambers of the first row then of the last row;
 the fluidic chambers each comprising at least two functionalized slides;
 the mesofluidic device for each row comprising:
 an upper cover (310) comprising a flat edge region (311) and indentations (312) to cover the fluidic chambers, each indentation being in fluidic communication with a solution inlet orifice (313);
 the functionalized slides (320-330), each comprising a surface (321-331) turned towards the upper cover, each surface (321-331) covered with a functionalized region facing an indentation, and pierced with an outlet orifice (322-332);
 at least one spacer (340) arranged in a leaktight manner between the at least two functionalized slides (320-330) of each chamber, and comprising as many openings as the upper cover comprises indentations, each pair of indentation and opening defining a chamber; and a lower cover (350) comprising as many outlets (351) as the upper cover (310) comprises solution inlet orifices (313), wherein the at least two functionalized slides of at least one fluidic chamber have a surface functionalized with molecules, at least some of which are able to form a bond with a receptor molecule borne by the rare target cells.

2. The device as claimed in claim 1, comprising at least one intermediate row (120) of fluidic chambers (121) equal in number to the number of chambers (111) of the first row (110), each fluidic chamber (121) of an intermediate row (120) comprising an inlet (122) fluidically connected to an outlet (113) of a chamber of the first row (110), and an outlet (123).

3. The device as claimed in claim 1, in which:
the functionalized slides of the chambers of the first row are provided with molecules capable of selectively binding to one or more cell population(s) of the sample other than the rare target cells;
the functionalized slides of the chambers of the last row are provided with different types of molecules capable of selectively forming a bond with the receptor molecule borne by the rare target cells.

4. The device as claimed in claim 1, in which the fluidic chambers (111) of the first row are connected to the reservoir of the biological solution via a single liquid supply channel, consisting of as many channel segments as fluidic chambers (111), the segments of the supply channel being of different, and increasingly small, sections in a direction of circulation of the liquid, each segment being in fluid communication with the solution inlet orifice of a fluidic chamber (111) to cause the liquid to enter into each fluidic chamber.

5. The device as claimed in claim 1, wherein the upper cover is provided with a liquid supply channel and connected to the reservoir of the biological solution, and wherein the liquid supply channel further comprises as many channel segments as the cover comprises indentations, the segments of the supply channel being of different, and increasingly small, sections in the direction of circulation of the liquid, each segment being in fluid communication with the inlet of a fluidic chamber to cause the liquid to circulate in the fluidic chambers.

6. The device as claimed in claim 1, in which the upper cover is transparent.

7. The device as claimed in claim 1, in which the upper cover is made of cyclic olefin copolymer.

8. The device as claimed in claim 1, wherein the device comprises a second row of fluidic chambers equal in number to the number of the fluidic chambers of the first and last row, wherein, in which the inlets of the fluidic chambers of each row, from the second row, are connected to the outlets of the fluidic chambers of the preceding row via tubes less than 5 cm in length.

9. The device as claimed in claim 1, in which the functionalized slides are transparent.

10. The device as claimed in claim 1, in which each of the functionalized slides comprises a visual code (220) which can be interpreted by a computer, the code comprising information relating to the molecules of the functionalized region of each of the functionalized slides.

11. A process for selective, specific and simultaneous sorting of rare target cells in a biological sample at a concentration of between 1 and 10 cells per milliliter (ml) of sample, comprising the following steps:
a) providing the mesofluidic device of claim 1,
wherein the inlets of the fluidic chambers of the first row are connected to the reservoir of the biological solution containing the rare target cells to sort, and the outlets of the fluidic chambers of the last row are connected to the at least one reservoir for collecting the solution;
b) causing the biological sample to circulate in the fluidic chambers, from the first row to the last row, so as to at least bind the rare target cells to the receptor molecules capable of selectively binding to the rare target cells;
c) analyzing surfaces of the functionalized slides containing the target cells bound in step b).

12. The process as claimed in claim 11, wherein step (b) further comprises:
functionalizing regions of the functionalized slides of the first row with molecules capable of selectively binding to one or more of cell population(s) in the sample other than the rare target cells;
functionalizing regions of the functionalized slides of row(s) following the first row with different types of molecules capable of selectively binding to a population or populations of the rare target cells, each functionalized region comprising a single type of said molecules.

* * * * *